(12) United States Patent
Gasper

(10) Patent No.: US 9,669,125 B2
(45) Date of Patent: Jun. 6, 2017

(54) METHODS OF EMITTING A VOLATILE MATERIAL FROM A DIFFUSER

(75) Inventor: Thomas P. Gasper, Germantown, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 673 days.

(21) Appl. No.: 12/886,048

(22) Filed: Sep. 20, 2010

(65) Prior Publication Data

US 2011/0068190 A1   Mar. 24, 2011

Related U.S. Application Data

(60) Provisional application No. 61/244,285, filed on Sep. 21, 2009.

(51) Int. Cl.
| | |
|---|---|
| *A01G 13/06* | (2006.01) |
| *F24F 6/00* | (2006.01) |
| *A61L 9/03* | (2006.01) |
| *A61L 9/12* | (2006.01) |

(52) U.S. Cl.
CPC ............... *A61L 9/035* (2013.01); *A61L 9/125* (2013.01); *A61L 9/037* (2013.01); *A61L 9/127* (2013.01)

(58) Field of Classification Search
USPC .......... 392/386, 387, 390–395; 261/DIG. 65, 261/DIG. 81; 239/303, 304, 305; 422/123
See application file for complete search history.

(56) References Cited

U.S. PATENT DOCUMENTS

| | | | |
|---|---|---|---|
| 3,410,488 | A | 11/1968 | Sugimura |
| 3,948,445 | A | 4/1976 | Andeweg |
| 4,425,302 | A | 1/1984 | Pons Pons |
| 4,603,030 | A | 7/1986 | McCarthy |
| 4,849,606 | A | 7/1989 | Martens, III et al. |
| 4,924,068 | A | 5/1990 | Henri |
| 5,029,729 | A | 7/1991 | Madsen et al. |
| 5,111,477 | A | 5/1992 | Muderlak et al. |
| 5,175,791 | A | 12/1992 | Muderlak et al. |
| 5,297,988 | A | 3/1994 | Nishino et al. |
| 5,591,395 | A | 1/1997 | Schroeder et al. |
| 5,591,409 | A | 1/1997 | Watkins |
| 5,647,053 | A | 7/1997 | Schroeder et al. |
| 5,937,140 | A | 8/1999 | Leonard et al. |
| 6,204,623 | B1 | 3/2001 | Levy et al. |

(Continued)

FOREIGN PATENT DOCUMENTS

| | | |
|---|---|---|
| EP | 1214949 | 6/2002 |
| EP | 1407790 | 4/2004 |

(Continued)

OTHER PUBLICATIONS

PCT/US2010/002558 International Search Report Dated Dec. 14, 2010.

(Continued)

*Primary Examiner* — Thor Campbell

(57) ABSTRACT

A method of emitting two or more volatile materials from a diffuser includes the step of emitting a first volatile material using a first diffusion element for a first randomly determined period of time. The method further includes the step of emitting a second volatile material using a second diffusion element for a section randomly determined period of time.

20 Claims, 5 Drawing Sheets

(56) References Cited

U.S. PATENT DOCUMENTS

| | | |
|---|---|---|
| 6,390,453 B1 | 5/2002 | Frederickson et al. |
| 6,478,440 B1 | 11/2002 | Jaworski et al. |
| 6,581,915 B2 | 6/2003 | Bartsch et al. |
| 6,603,924 B2 | 8/2003 | Brown et al. |
| 6,661,967 B2 | 12/2003 | Levine et al. |
| 6,712,287 B1 * | 3/2004 | Le Pesant et al. ............ 239/67 |
| 6,790,408 B2 | 9/2004 | Whitby et al. |
| 6,792,199 B2 | 9/2004 | Levine et al. |
| 6,854,717 B2 | 2/2005 | Millan |
| 6,857,580 B2 | 2/2005 | Walter et al. |
| 6,862,403 B2 | 3/2005 | Pedrotti et al. |
| 6,917,754 B2 | 7/2005 | Pedrotti et al. |
| 6,920,282 B2 | 7/2005 | He et al. |
| 6,923,383 B1 | 8/2005 | Joshi et al. |
| 6,931,202 B2 | 8/2005 | Pedrotti et al. |
| 6,996,335 B2 | 2/2006 | Zobele |
| 7,036,800 B2 | 5/2006 | Ellis |
| 7,223,361 B2 * | 5/2007 | Kvietok et al. ................ 422/4 |
| 7,249,719 B2 | 7/2007 | He et al. |
| 7,484,716 B2 | 2/2009 | Morie et al. |
| 7,493,028 B2 | 2/2009 | DeWitt et al. |
| 2004/0028551 A1 * | 2/2004 | Kvietok et al. ................ 422/4 |
| 2004/0033171 A1 * | 2/2004 | Kvietok et al. ............ 422/123 |
| 2004/0101447 A1 | 5/2004 | Tajima et al. |
| 2004/0265164 A1 * | 12/2004 | Woo et al. .................... 422/5 |
| 2005/0205916 A1 | 9/2005 | Conway et al. |
| 2006/0193611 A1 | 8/2006 | Ruiz Ballesteros et al. |
| 2007/0012718 A1 | 1/2007 | Schramm et al. |
| 2007/0160492 A1 | 7/2007 | Spector |
| 2007/0166185 A1 | 7/2007 | Bartels |
| 2007/0166186 A1 | 7/2007 | Stec |
| 2007/0280653 A1 | 12/2007 | Viera |
| 2008/0014125 A1 | 1/2008 | He et al. |
| 2008/0095522 A1 | 4/2008 | Deflorian et al. |
| 2008/0191370 A1 | 8/2008 | Pankhurst et al. |

FOREIGN PATENT DOCUMENTS

| | | |
|---|---|---|
| GB | 2443925 | 5/2008 |
| JP | 5173648 | 7/1993 |
| WO | 2007064189 | 6/2007 |
| WO | 2007079046 | 7/2007 |
| WO | 2008149065 | 12/2008 |

OTHER PUBLICATIONS

PCT/US2010/002558 International Search Report dated Apr. 2, 2012.

* cited by examiner

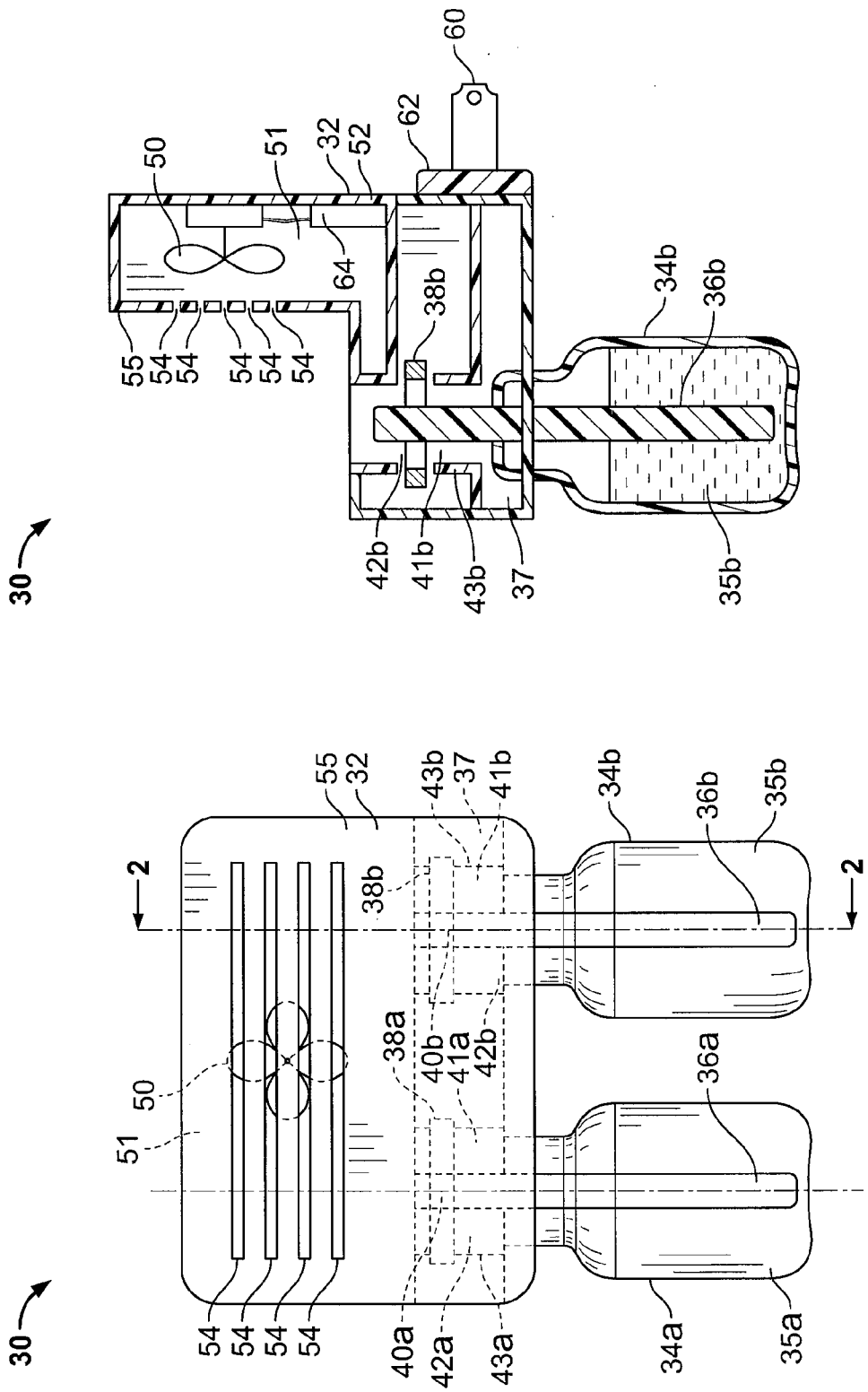

METHODS OF EMITTING A VOLATILE MATERIAL FROM A DIFFUSER

CROSS REFERENCE TO RELATED APPLICATIONS

This application claims the benefit of Gasper U.S. Provisional Application Ser. No. 61/244,285, filed Sep. 21, 2009, and entitled "Volatile Material Dispenser."

REFERENCE REGARDING FEDERALLY SPONSORED RESEARCH OR DEVELOPMENT

Not applicable

SEQUENTIAL LISTING

Not applicable

BACKGROUND

1. Field of the Invention

The present invention relates to volatile material diffusers, and more particularly, to volatile material diffusers for dispensing one or more volatile materials from one or more containers.

2. Description of the Background

A multitude of volatile material diffusion devices or diffusers exist in the marketplace. Many of such devices are passive devices that require only ambient air flow to disperse the liquid active material therein. Other devices are battery-powered or receive household power via a plug extending from the device. A cord may be coupled between the plug and the device, or the plug may be mounted directly on the device.

Various means for dispensing volatile materials from volatile material diffusers are also known in the art. For example, some diffusers include a heating element for heating a volatile material to promote vaporization thereof. Other diffusers employ a fan or blower to generate air flow to direct volatile material out of the diffuser into the surrounding environment. In another type of diffuser, one or more volatile materials may be emitted from the diffuser using a bolus generator that delivers a pulse of air to eject a scent ring. Still other diffusers that dispense volatile materials utilize ultrasonic means to dispense the volatile materials therefrom. In addition, other diffusers utilize more than one of these means to vaporize and/or disperse volatile materials.

In the past, such means have been utilized to dispense one or more volatile materials from a single diffuser. Multiple volatile materials have been used to prevent habituation, which is a phenomenon that occurs when a person becomes used to a particular volatile material such that they no longer perceive that volatile material.

One such device for emitting multiple volatile materials includes a multi-aroma cartridge having a frame with sections containing absorbent material saturated with different fragrances. The cartridge is inserted into a device having heaters disposed beneath each of the sections containing absorbent material. The heaters are actuated to dispense different fragrances.

One multi-fragrancing device includes two containers each having a wick extending therefrom and in contact with fragrances with the containers. Ring heaters are disposed around each of the wicks to vaporize fragrance disposed within the respective wicks. Energy is continuously supplied to a first of the heaters to continuously supply a first of the fragrances and energy is intermittently supplied to a second of the heaters to intermittently supply a second of the fragrances. The intermittent supply of the second fragrance prevents habituation with respect to the first fragrance by periodically supplying the second fragrance.

A further multi-fragrancing device includes first and second containers having first and second wicks respectively extending therefrom and in contact with first and second volatile materials disposed in the first and second containers, respectively. First and second heaters are disposed adjacent the first and second wicks, respectively, wherein the first and second heaters are alternately energized to alternately vaporize and disperse the first and second fragrances. In this device, the alternation of fragrances for a period of time, such as between 15 minutes and 2 hours, prevents habituation with respect to both of the fragrances.

Another multi-fragrancing device utilizes both heat and air flow to vaporize and disperse fragrances. Two containers having wicks extending therefrom and in contact with fragrances in the containers are disposed within the device. One or more heaters are disposed adjacent the wicks and one or more fans are disposed behind the wicks. A wall is disposed above the wicks to allow vaporized fragrance therethrough for dispersion by the one or more fans. The wall prevents air flow from the fan from cooling the heaters and/or wicks.

SUMMARY OF THE INVENTION

In a first aspect of the present invention, a method of emitting two or more volatile materials from a diffuser includes the step of emitting a first volatile material using a first diffusion element for a first randomly determined period of time. The method further includes the step of emitting a second volatile material using a second diffusion element for a second randomly determined period of time.

In a further aspect of the present invention, a method of emitting two or more volatile materials from a diffuser includes the steps of emitting a first volatile material for a first current emission time period and emitting a second volatile material for a second current emission time period. At least one of the first and second current emission time periods is defined by the equation: CURRENT EMISSION TIME PERIOD=BASE TIME PERIOD+INCREMENTAL TIME PERIOD.

In yet a another aspect of the present invention, a method of emitting two or more volatile materials from a diffuser includes the step of emitting a first volatile material for a first current emission time period that is comprised of a first base time period and a first incremental time period, wherein the incremental time period is determined randomly. The method further includes the step of emitting a second volatile material for a second current emission time period that is comprised of a second base time period and a second incremental time period, wherein the second incremental time period is determined randomly and the first and second base time periods are the same.

BRIEF DESCRIPTION OF THE DRAWINGS

FIG. 1 is a diagrammatic representation of a first embodiment of a volatile material diffuser;

FIG. 2 is a cross-sectional view taken generally along the lines 2-2 of FIG. 1;

Other aspects and advantages of the present invention will become apparent upon consideration of the following detailed description and the attached drawings, in which like elements are assigned like reference numerals.

DETAILED DESCRIPTION

Figure 3:
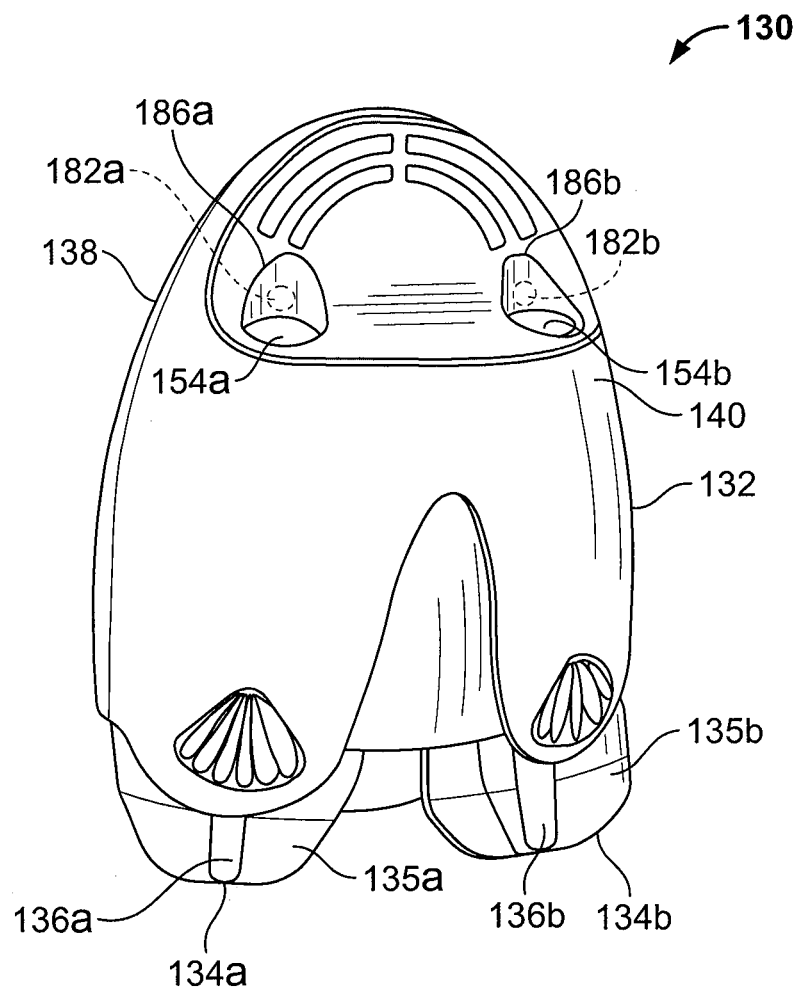
FIG. 3 is a front isometric view of a second embodiment of a volatile material diffuser.

Referring to FIGS. 1 and 2, a volatile material diffuser 30 generally includes a housing 32. Two containers 34a, 34b having volatile materials 35a, 35b therein and wicks 36a, 36b in contact with the volatile materials 35a, 35b and extending out of the containers 34a, 34b are adapted to be inserted within the housing 32. The containers 34a, 34b may be inserted into and retained within the housing 32 by any means known in the art.

Referring again to FIGS. 1 and 2, the volatile material diffuser 30 includes a first chamber 37 having heaters 38a, 38b disposed adjacent the wicks 36a, 36b for vaporization of the volatile materials 35a, 35b, which move by capillary action through the wicks 36a, 36b to top portions 40a, 40b of the wicks 36a, 36b. The wicks 36a, 36b and heaters 38a, 38b reside within channels 41a, 41b (only 41b shown) formed within the first chamber 37. The channels 41a, 41b have a diameter that is greater than a diameter of the wicks 36a, 36b to provide a gap 42a, 42b (only 42b shown) between the wicks 36a, 36b and cylindrical walls 43a, 43b (only 43b shown) forming the respective channels 41a, 41b.

An optional fan 50 is disposed within a second chamber 51 in a rear portion 52 of the housing 32 and slots or vents 54 are disposed opposite the fan 50 in a front wall 55 forming the chamber 51. The fan 50 may be operated such that energy is continuously supplied thereto. Alternatively, energy may be supplied intermittently to the fan 50 to create intermittent flows of air. Optionally, separate fans may be utilized in combination with each of the heaters 38a, 38b.

Still referring to FIGS. 1 and 2, the diffuser 30 preferably, although not necessarily, has two electrical blades 60 (only one shown) extending from a rear side 62 thereof for insertion into a common electrical socket. In this manner, the diffuser 30 is supplied direct current to operate a controller 64 (FIG. 2), the heaters 38a, 38b, and the fan 50. Optionally, the diffuser 30 may be battery-operated.

Figure 4:
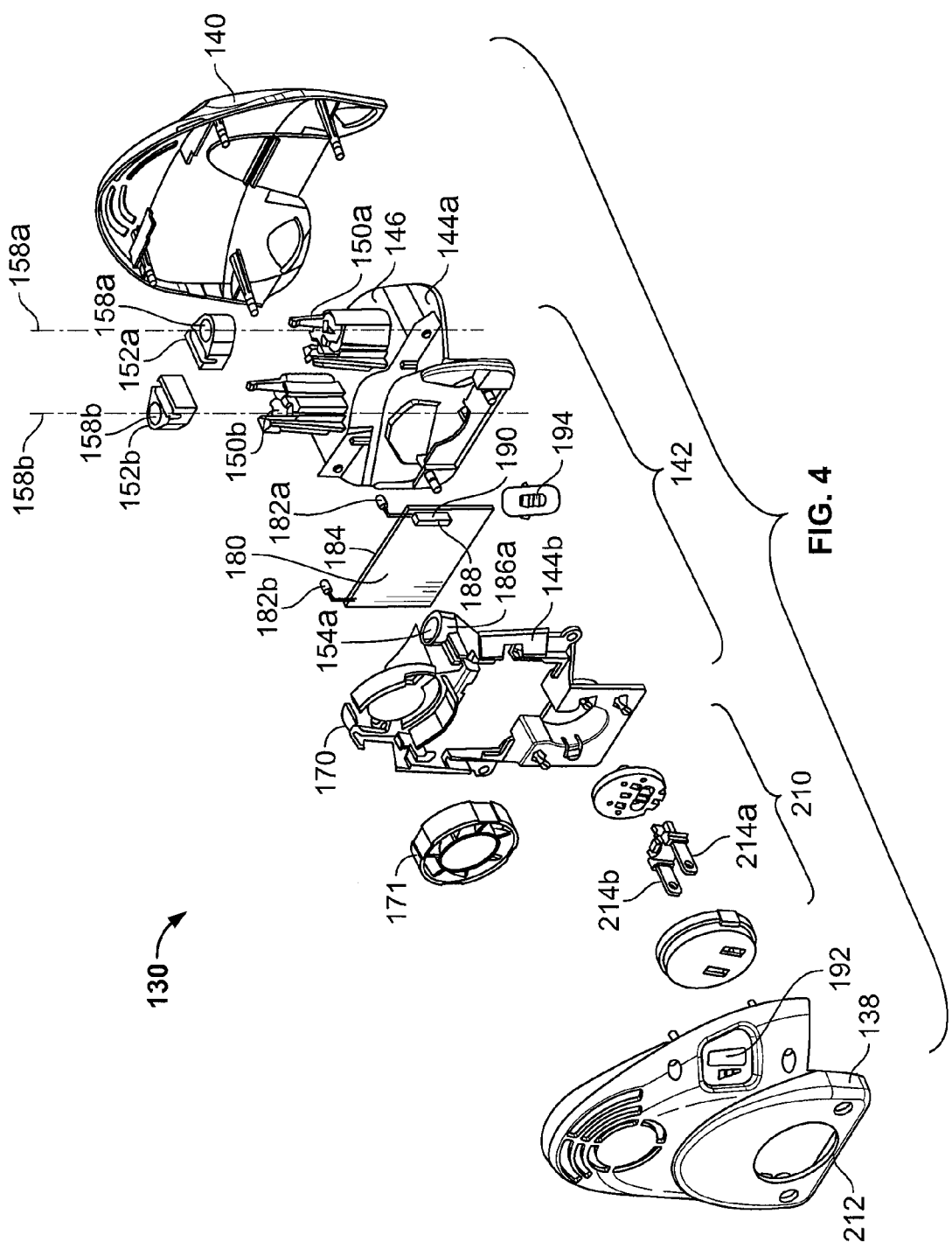
FIG. 4 is an exploded view of the diffuser of FIG. 3.

A further embodiment of a volatile material diffuser 130 is depicted in FIGS. 3 and 4. The diffuser 130 is similar to and works in manner similar to the diffuser 30 of FIGS. 1 and 2. The diffuser 130 includes a housing 132 for holding two containers 134a, 134b having volatile materials 135a, 135b therein and wicks 136a, 136b extending therefrom. As best seen in FIG. 4, the housing 132 includes a rear portion 138, a cover portion 140, and a mounting structure 142. The mounting structure 142 is attached to the rear portion 138 and the cover portion 140 is mounted to the rear portion 138 and the mounting structure 142 such that the mounting structure 142 is disposed between the rear and cover portions 138, 140. Referring to FIG. 4, the mounting structure 142 includes front and rear portions 144a, 144b, wherein the front portion 144a includes a horizontal surface 146 having first channels 150a, 150b extending therethrough, ring heaters 152a, 152b disposed atop structures forming the first channels 150a, 150b, and second channels 154a, 154b positioned over the ring heaters 152a, 152b. The heaters 152a, 152b are disposed above the first channels 150a, 150b, and the second channels 154a, 154b are disposed above the heaters 152a, 152b. A fan supporting structure 170 having a fan 171 therein extends upwardly from the rear portion 144b of the mounting structure 142 above the second channels 154a, 154b.

As seen in FIG. 4, a controller in the form of a printed circuit board (PCB) 180 is secured within the rear portion 144b of the mounting structure 142 and includes all circuitry to control the diffuser 130. First and second light sources 182a, 182b extend from an upper edge 184 of the PCB 180 and are disposed adjacent rear surfaces 186a, 186b of the second channels 154a, 154b. When the light sources 182a, 182b are illuminated, the light can be seen through the rear surfaces 186a, 186b, respectively. The light sources 182a, 182b may be illuminated when respective heaters 152a, 152b are actuated. In one embodiment, the light sources 182a, 182b are illuminated at a fixed or constant intensity to indicate which of the heaters 152a, 152b is activated. In a further embodiment, the intensity of the light sources 182a, 182b may change over time to indicate which of the heaters 152a, 152b is activated. In particular, one or more of the light sources 182a, 182b may start off at a low intensity and slowly increase in intensity until a high intensity is reached, and thereafter decrease in intensity until the low intensity is reached and continuously cycle through high and low intensities (to simulate breathing or a heartbeat). Alternatively, the intensity may start off at a high intensity and slowly decrease until the low intensity is reached and, again, cycle through high and low intensities. Still alternatively, one or more of the light sources 182a, 182b may initially be illuminated at a higher or lower intensity and may thereafter cycle back and forth between the higher and lower intensities. One or more of the light sources 182a, 182b may be disposed at any location within the diffuser 130. The light sources 182a, 182b are preferably, although not necessarily, light emitting diodes (LEDs).

Still referring to FIG. 4, an intensity selector switch 188 extends from the PCB 180 and includes an actuator arm 190 that extends through an aperture 192 in the rear portion 138 of the housing 132. A button 194 is disposed over the actuator arm 190 to change a position of the switch 188. The position of the switch 188 is sensed by the PCB 180 and an intensity level at which the volatile materials 135a, 135b are emitted is varied based on the position of the switch 188. The intensity may be varied by changing a level of heat output by the heaters 152a, 152b. In one embodiment, if three intensity levels are utilized, temperatures of the heaters 152a, 152b would be set to 55° C. for a first or lowest setting, 65° C. for a second or middle setting, and 75° C. for a third or highest setting. In a further embodiment employing three intensity levels, temperatures of the heaters 152a, 152b would be set to 50° C. for the first setting, 60° C. for the second setting, and 70° C. for the third setting. Although three intensity levels are described, any number of intensity levels may be employed. In a further embodiment, a random number generator may be used to determine a random intensity level or heater temperature, as discussed in more detail hereinbelow. Still further, the switch 188 may also be replaced by a dial, an LCD screen, one or more buttons, and/or any other know device that would allow a user to adjust a characteristic of a diffusion element or of a component of the diffuser.

The light sources 182a, 182b and intensity level switch 188 of the diffuser 130 of FIGS. 3 and 4 may be utilized with any of the embodiments herein or any diffuser for dispensing one or more volatile materials.

As seen in FIG. 4, a plug assembly 210 is connected to the rear portion 144b of the mounting structure 142 and extends through an aperture 212 in the rear portion 138 of the housing 132. Electrical blades 214a, 214b of the plug assembly 210 are inserted into an electrical socket to power the diffuser 130.

Referring to FIG. 4, the containers 134a, 134b, as seen in FIG. 25 are inserted into the diffuser 130 by inserting portions of the wicks 136a, 136b that extend out of the respective containers 134a, 134b through the first channels 150a, 150b and the ring channels 156a, 156b, respectively, such that the wicks 136a, 136b reside in same and gaps are formed between the wicks 136a, 136b and walls forming the first channels 150a, 150b and the ring channels 156a, 156b.

The diffusers 30 of FIGS. 1 and 2 and 130 of FIGS. 3 and 4 are more fully disclosed in Porchia et al. U.S. application Ser. No. 11/427,714, entitled "Volatile Material "Diffuser and Method of Preventing Undesirable Mixing of Volatile Materials," the disclosure of which is hereby incorporated by reference in its entirety.

Figure 5:
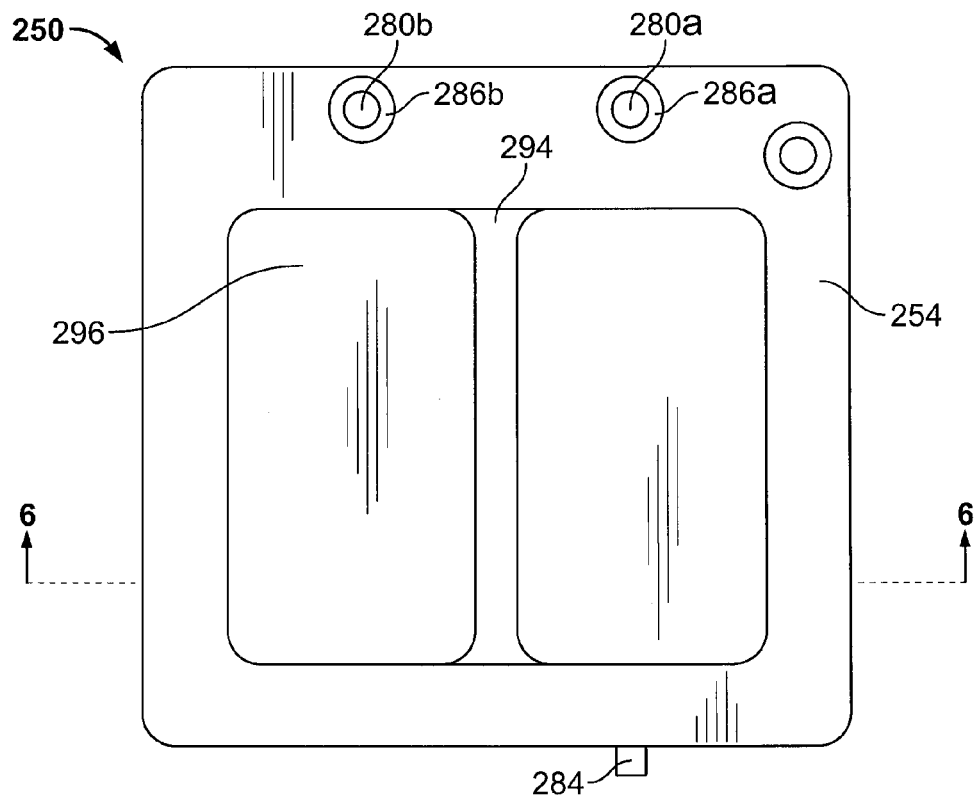
FIG. 5 is a front elevational view of a further embodiment of a volatile material diffuser.
Figure 6:
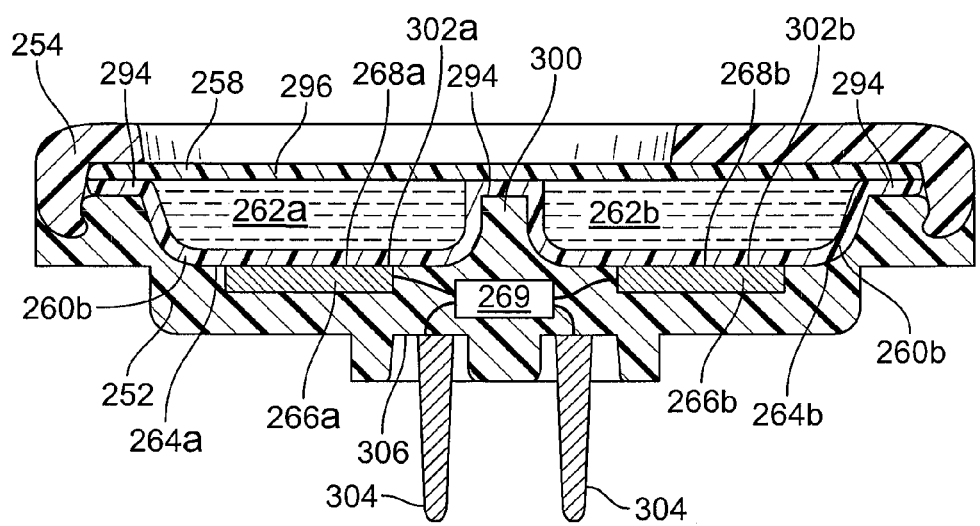
FIG. 6 is a cross-sectional view taken generally along the line 6-6 of FIG. 5.

Referring to FIGS. 5 and 6, a further diffuser 250 generally includes a base portion 252 and a modular decorative cover portion 254. The base portion 252 includes a plurality of heating pans 264a, 264b. A heater or heating element 266a, 266b is centrally disposed within each heating pan 264a, 264b such that an exposed surface 268a, 268b of the heating element 266a, 266b is approximately flush with the surrounding surface of the heating pan 264a, 264b. Each heating element 266a, 266b is independently controllable by a controller 269 (FIG. 6) disposed in the base portion 252.

Referring to FIG. 5, the base portion 252 may include one or more light sources 280a, 280b, each disposed proximate to a corresponding heating pan 264a, 264b. The one or more light sources 280a, 280b are illustrated as disposed on the base portion 252 and visible through one or more corresponding lighting orifices 286a, 286b when the cover portion 254 is attached to the base portion 252. The light sources 280a, 280b are similar to the light sources 182a, 182b of FIGS. 3 and 4.

Referring to FIG. 5, the base portion 252 may also include an intensity selector switch 284, for example, in electrical communication with the controller 269 and disposed along a bottom edge as illustrated. The switch 284 may include a plurality of settings each corresponding to an intensity of heat that would be applied by the heating elements 266a, 266b of the volatile material diffuser 250.

Referring to FIG. 6, the volatile material holder 258 includes a plurality of independent reservoirs 260a, 260b. Each of the plurality of independent reservoirs 260a, 260b includes a volatile material 262a, 262b therein and is entirely surrounded by a flange 294. A non-porous permeable membrane 296 is adhered to the flange 294 to cover each of the plurality of reservoirs 260a, 260b and extends across the volatile material holder 258. The volatile material holder 258 is similar to the volatile material holders described in U.S. Pat. No. 7,441,360, which is herein incorporated by reference in its entirety. The impermeable laminate 298 is removed from the volatile material holder 258 before use.

A surface 268a, 268b of each heating element 266a, 266b is spaced from or makes contact with a bottom surface 302 of each independent reservoir 260a, 260b, as shown in FIG. 6. Each of the independent reservoirs 260a, 260b is heated by independent application of power via the controller 269 to each of the heating elements 266a, 266b to accelerate diffusion of the volatile material 262a, 262b into the atmosphere. The heating elements 266a, 266b are thermally isolated from one another by a wall 300 therebetween. Thermal isolation between the heating elements 266a, 266b helps to minimize thermal cross-talk between the heating pans 264a, 264b, which allows more precise independent control of the volatilization of the volatile material 262a, 262b from each of the independent reservoirs 260a, 260b.

Referring to FIG. 6, the base portion 252 further includes electrical prongs 304 that are in electrical communication with the controller 269 and extend substantially perpendicularly from a rear surface 306 of the base portion 252. The electrical prongs 304 are adapted to be inserted into a wall outlet to provide power to the diffuser 250.

The diffuser 250 of FIGS. 5 and 6, and additional similar diffusers, are more fully disclosed in Neumann et al. U.S. application Ser. No. 12/319,606, entitled "Fragrance Dispenser," the disclosure of which is hereby incorporated by reference in its entirety.

The volatile materials in any of the diffusers 30, 130, 250 may be the same or different volatile materials and also may of the same type or different types. The different types of volatile materials that may be used include, for example, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Two volatile materials of the same type need not be utilized. For example, an insecticide and a fragrance may be used, a disinfectant and a repellent may be used, or any other combination of types of volatile materials may be used.

The diffusers 30, 130, and 250 as disclosed herein preferably operate in a manner that prevents habituation to a particular volatile material 35a, 35b, 135a, 135b, and 262a, 262b, if a fragrance or the like is used. The volatile materials 35a, 35b, 135a, 135b, and 262a, 262b are preferably emitted in an alternating sequence. In particular, one or more modes of operation may be implemented by the controllers 64, 180, 269 to control an amount and a temporal distribution of power distributed to the heaters 38a, 38b, 152a, 152b, 266a, 266b. Although the modes of operation disclosed herein are discussed with respect to heaters, such modes of operation may be implemented for other diffusion elements, as discussed in greater detail hereinbelow.

In a first mode of operation, when the diffuser 30 is plugged into an electrical socket, a first of the heaters 38a, 152a, 266a is activated to emit a first of the volatile materials 35a, 135a, 262a. After a first period of time, the first heater 38a, 152a, 266a is deactivated and a second of the heaters 38b, 152b, 266a is activated for a second period of time to emit a second of the volatile materials 35b, 135b, 262b. After the second period of time, the second heater 38b, 152b, 266b is deactivated, the first heater 38a, 152a, 266a is activated, and the sequence repeats until the diffuser 30, 130, 250 is unplugged from the electrical socket. In this sequence, the first and second heaters 38a, 38b, 152a, 152b, or 266a, 266b are activated and deactivated simultaneously. Alternatively, in a second mode of operation, a third period of time may elapse between deactivation of one of the heaters 38a, 38b, 152a, 152b, or 266a, 266b and activation of the next heater 38a, 38b, 152a, 152b, or 266a, 266b, thereby having no heater activated for the third period of time. Still alternatively, in a third mode of operation, a fourth period of time may elapse between the activation of one of the heaters 38a, 38b and the deactivation of the other heater 38a, 38b, 152a, 152b, or 266a, 266b, thereby creating an overlap of volatile materials 35a, 35b, 135a, 135b, or 262a, 262b for the fourth period of time.

In the first, second, and third modes of operation, the first and second periods of time may be the same such that each heater 38a, 38b, 152a, 152b, or 266a, 266b is activated for an equivalent period of time. Alternatively, the first and second periods of time may be different. The first and second periods of time may be between about 10 seconds and about 8 hours, more preferably between about 15 minutes and about 2 hours, and most preferably about 30 minutes, about 60 minutes, or about 90 minutes.

The controller 64, 180, 269 of any of the embodiments herein or any multi-fragrancing device may implement any alternating sequence of volatile materials, such as those described with respect to the first, second, and third modes of operation, with a random number generator and a timer to operate a fourth mode of operation. The controller 64, 180, 269 is in the form of programmable device, such as an application specific integrated circuit (ASIC), a microcontroller, or the like.

Figure 7:
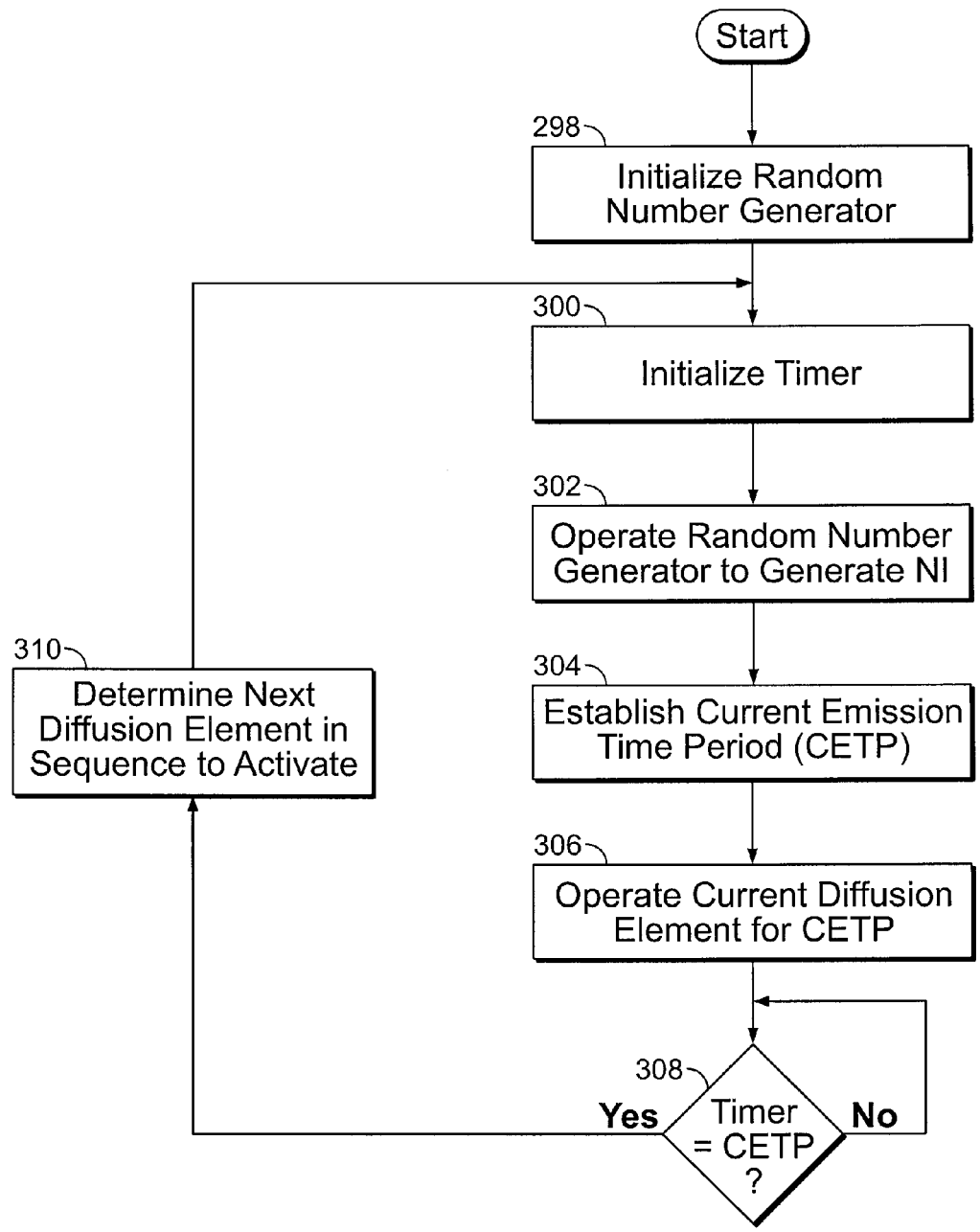
FIG. 7 is a flow chart illustrating programming of a fourth mode of operation that may be implemented by a programmable device for operation of various volatile material diffusers.

FIG. 7 depicts programming for the fourth mode of operation that is implemented by the programmable device. In the fourth mode of operation, emission of volatile materials is alternated as described in detail with respect to any of the first, second, or third embodiments. The fourth mode of operation randomly varies the emission time periods and/or time periods during which the volatile materials are emitted. Optionally, if the second mode of operation is utilized, the third period of time (in which no diffusion element is activated), may be randomly varied or, if the third mode of operation is utilized, the fourth period of time (in which both diffusion elements are activated), may be randomly varied.

Referring to FIG. 7, operation begins at a block 298 after the diffuser 30, 130, or 250 is plugged into an electrical outlet, wherein the block 298 initializes the random number generator and a block 300 initializes and starts the timer. Next, control passes to a block 302 that operates the random number generator to generate a random number N1. Control then passes to a block 304 that establishes a current emission time period (CETP) for the current volatile material in the sequence. The current emission time period is determined and set in part based on the number N1 selected by the random number generator as follows:

CURRENT EMISSION TIME PERIOD=BASE TIME PERIOD+(N1×TIME FACTOR);

wherein (N1×TIME FACTOR) is defined as an INCREMENTAL TIME PERIOD

For example, in one embodiment, the range of current emission time periods may be between about 45 minutes and about 120 minutes. In such case, a more specific equation used to determine the current emission time period may be:

CURRENT EMISSION TIME PERIOD=45 minutes+(N1×5 minutes);

where 0<=N1<=15.

Using this equation with the base time period being 45 minutes and the time factor being 5 minutes, a minimum emission time period of 45 minutes is established and set if N1 is randomly selected to be 0 and a maximum emission time period of 120 minutes is established and set if N1 is randomly selected to be 15, with a number of potential random emission time periods therebetween.

In a further exemplary embodiment, a range of current emission time periods may be between about 30 minutes and about 8 hours. In such case, a more specific equation used to determine the current emission time period may be:

CURRENT EMISSION TIME PERIOD=30 minutes+(N1×10 minutes)

where 0<=N1<=45.

Using this equation with the base time period being 30 minutes and the time factor being 10 minutes, a minimum emission time period of 30 minutes is established and set if N1 is randomly selected to be 0 and a maximum emission time period of 480 minutes (or 8 hours) is established and set if N1 is randomly selected to be 45, with a number of potential random emission time periods therebetween.

Although specific embodiments of the equation for determining the current emission time period are disclosed herein, a number of variations are possible. For example, the base time period is preferably programmed to be the minimum desired current emission time period, which is preferably between about 10 seconds and about 8 hours, more preferably between about 5 minutes and about 4 hours, and most preferably between about 45 minutes and about 2 hours. In addition, the time factor is preferably set to any number between about 10 seconds and about 8 hours, more preferably between about 1 minute and 60 minutes, and most preferably between about 5 minutes and about 30 minutes.

Once the current emission time period is set at the block 304 for a particular emission of a volatile material, control passes to a block 306 wherein a diffusion element associated with the current volatile material is activated for the current emission time period. A block 308 then determines whether the current emission time period has elapsed and control remains with the block 308 until the current emission time period has elapsed. Once the block 308 determines that the current emission time period has elapsed, control passes to a block 310 that determines which diffusion element is next in the sequence. After the block 310, control returns to the block 302 where the random number generator generates a number N1 and operation continues to cycle through the loop of FIG. 7 including the blocks 300, 302, 304, 306, 308, and 310 for the next diffusion element in the sequence, and thus the next volatile material. The loop is repeated continuously, alternating among diffusion elements and volatile materials according to the programmed sequence, until the diffuser 30, 130, and 250 is unplugged.

Diffusion element(s) as referred to in FIG. 7 may be any type of element that promotes diffusion of a volatile material. Examples of diffusion elements include, but are not limited to, aerosol actuators, piezoelectric elements, heaters, fans, nebulizers, and the like. To that effect, any of the modes of operation disclosed herein may be utilized with any type of diffusion element and/or combinations of diffusion elements (e.g. a device that utilizes multiple heaters and a single fan, a device that utilizes a heater to diffuse a first volatile material and a fan to diffuse a second material, etc.).

The modes of operation disclosed herein may be utilized for any diffuser that emits two or more volatile materials. In particular, any number of volatile materials may be emitted. In addition, such modes may be utilized to diffuse volatile materials in any form, such as aerosols, gels, liquids, solids, and the like.

INDUSTRIAL APPLICABILITY

The present invention provides volatile material diffusers for emitting at least one volatile material therefrom, wherein, if multiple volatile materials are emitted, the volatile materials are emitted in an alternating sequence. The volatile materials are disclosed as being vaporized by heaters, fans, or any other known diffusion element. Various modes of operation are disclosed for alternating the volatile materials in order to limit or prevent habituation. One or more LEDs may be incorporated into a diffuser to indicate which volatile material(s) is being emitted.

Numerous modifications will be apparent to those skilled in the art in view of the foregoing description. Accordingly, this description is to be construed as illustrative only and is presented for the purpose of enabling those skilled in the art to make and use the present application and to teach the best mode of carrying out same. All patents and other references cited herein are incorporated by reference in their entirety. The exclusive rights to all modifications which come within the scope of the appended claims are reserved.

I claim:

1. A method of emitting two or more volatile materials from a diffuser, the method comprising the steps of:
    initializing a random number generator;
    determining, via the random number generator, a first random number;
    establishing a first current emission time period, wherein the first current emission time period is based, in part, on the first random number;
    emitting a first volatile material using a first diffusion element for the first emission time period;
    determining, via the random number generator, a second random number;
    establishing a second current emission time period, wherein the second current emission time period is based, in part, on the second random number; and
    emitting a second volatile material using a second diffusion element for the second emission time period,
    wherein each of the first current emission time period and the second current emission time period is between a minimum current emission time period and a maximum emission time period.

2. The method of claim 1, wherein the first and second diffusion elements are heaters.

3. The method of claim 1, wherein the first and second diffusion elements are fans.

4. The method of claim 1, wherein the first current emission time period and the second current emission time period do not overlap.

5. The method of claim 1, wherein at least one of the first diffusion element and the second diffusion element is a heater or at least one of the first diffusion element and the second diffusion element is a fan.

6. A method of emitting two or more volatile materials from one or more diffusers, the method comprising the steps of:
    initializing a random number generator;
    determining, via the random number generator, a first random number;
    activating a first diffuser to emit a first volatile material for a first current emission time period, which is based, in part, on the first random number;
    deactivating the first diffuser for a first non-emission time period;
    determining, via the random number generator, a second random number;
    activating a second diffuser to emit a second volatile material for a second current emission time period;
    determining the first and second current emission time periods by adding a randomly determined incremental time period to a base time period; and
    determining the incremental time period by multiplying the random numbers determined by the number generator by a time factor,
    wherein the random number is determined for each of the first and second current emission time periods.

7. The method of claim 6, further including the step of deactivating the second diffuser for a second non-emission time period.

8. The method of claim 6, wherein at least one of the first diffuser and the second diffuser is a heater that is used to dispense at least one of the first and second volatile materials.

9. The method of claim 6, wherein at least one of the first diffuser and the second diffuser is a fan that is used to dispense at least one of the first and second volatile materials.

10. The method of claim 6, wherein the first non-emission time period is predetermined.

11. The method of claim 6, wherein the first non-emission time period is determined randomly.

12. The method of claim 6, further including the steps of emitting a third volatile material for a third current emission time period and determining the first, second, and third current emission time periods by adding the randomly determined INCREMENTAL TIME PERIOD to the base time period.

13. The method of claim 6, wherein at least one of the first diffuser and the second diffuser is a heater that is used to dispense at least one of the first and second volatile materials.

14. A method of emitting two or more volatile materials from a diffuser, the method comprising the steps of:
    emitting a first volatile material for a first current emission time period that is comprised of a first base time period and a first incremental time period, wherein the incremental time period is determined randomly by a controller; and
    emitting a second volatile material for a second current emission time period that is comprised of a second base time period and a second incremental time period, wherein the second incremental time period is determined randomly by the controller and the first and second base time periods are the same and greater than 0,
    wherein each of the first current emission time period and the second current emission time period is between a minimum current emission time period and a maximum emission time period.

15. The method of claim 14, wherein the first and second volatile materials are emitted by activating first and second heaters, respectively, and wherein the method further includes the step of deactivating the first heater before activation of the second heater to create a period of time in which no heater is activated.

16. The method of claim 15, wherein the period of time in which no heater is activated is determined randomly.

17. The method of claim 14, wherein the first and second base time periods are predetermined and the first and second incremental time periods are determined randomly.

18. The method of claim 14, wherein the incremental time period is defined by a randomly determined number multiplied by a predetermined time factor.

19. The method of claim 18, wherein the base time period is set to between about 10 seconds and about 8 hours and the time factor is set to be between about 10 seconds and about 8 hours.

20. The method of claim 19, wherein the minimum current emission time period is about 45 minutes and the maximum current emission time period is about 120 minutes.

* * * * *